United States Patent [19]

Krier

[11] Patent Number: 5,731,503
[45] Date of Patent: Mar. 24, 1998

[54] INBRED CORN LINE NP 948

[75] Inventor: Merl Krier, Northfield, Minn.

[73] Assignee: Novartis Corporation

[21] Appl. No.: 716,836

[22] Filed: Aug. 22, 1996

Related U.S. Application Data

[63] Continuation of Ser. No. 336,627, Nov. 9, 1994, abandoned.
[51] Int. Cl.$^6$ .............................. A01H 5/00; A01H 4/00; C12N 5/04
[52] U.S. Cl. .................... 800/200; 800/235; 800/250; 800/DIG. 56; 435/412; 435/424; 435/430; 435/430.1; 47/58; 47/DIG. 1
[58] Field of Search .................................. 800/200, 205, 800/235, 250, DIG. 56; 435/240.1, 240.4, 240.47, 240.49, 240.5, 412, 424, 430, 430.1; 47/58, DIG. 1

[56] References Cited

U.S. PATENT DOCUMENTS 5,082,992  1/1992  Ambrose et al. ..................... 800/200

OTHER PUBLICATIONS

Coe et al. In Corn and Corn Improvement. Third Edition. Sprague et al., eds. Ch 3:81–137, Jan. 1988.

Hallauer et al. In Corn and Corn Improvement. Third Edition. Sprague et al. eds. Ch 8:463–564, Jan. 1988.

*Primary Examiner*—Gary Benzion
*Assistant Examiner*—Thanda Wai
*Attorney, Agent, or Firm*—Thomas Hoxie, Esq.

[57] ABSTRACT

An inbred corn line, designated NP 948, is disclosed. The invention relates to the seeds of inbred corn line NP 948, to the plants of inbred corn line NP 948 and to methods for producing a corn plant produced by crossing inbred line NP 948 with itself or with another corn plant. The invention further relates to hybrid corn seeds and plants produced by crossing inbred line NP 948 with another corn line. Particularly the invention provides novel hybrid corn plants, designated N2555 and N3030, produced by crossing inbred NP 948 with another Northrup King proprietary inbred corn line.

18 Claims, No Drawings

INBRED CORN LINE NP 948

This is a CONTINUATION of application Ser. No. 08/336,627, filed on Nov. 9, 1994, abandoned.

BACKGROUND OF THE INVENTION

This invention relates to a new and distinctive corn inbred line designated NP 948 and to hybrids made by using NP 948 as a parent. These hybrids include novel hybrids N2555 and N3030.

Corn is a valuable and important field crop. Thus, plant breeders are continually developing new and superior corn inbred lines for production of hybrids. The goal of the plant breeder is to maximize the amount of corn grain produced and to minimize the plant's susceptibility to environmental and pest stresses.

The development of corn hybrids requires the development of homozygous inbred lines, the crossing of these lines, and the subsequent evaluation of those crosses. Pedigree, backcross, and recurrent selection breeding methods are used to develop inbred lines from breeding populations. Breeding programs combine the genetic backgrounds from two or more inbred lines or various other genetic sources into breeding pools from which new inbred lines are developed by self pollination and selection of desired phenotypes. The new inbred lines are crossed with other inbred lines, and hybrids from these crosses are evaluated to determine which have commercial potential.

Once the inbred parents that give a superior hybrid are identified, the hybrid seed can be reproduced indefinitely as long as inbred parent homogeneity is maintained. Corn hybrids may be either single cross hybrids, produced when two inbred lines are crossed to produce the $F_1$ progeny; double cross hybrids, produced from four inbred lines crossed in pairs (A×B and C×D) and then the two $F_1$ hybrids are crossed again (A×B)×(C×D); or three-way cross hybrids produced from crossing a single cross (A×B) to a third inbred line C. Numerous references are available on the topic of corn breeding and hybrid seed corn production.

Those skilled in the art of corn breeding and production are well aware of techniques and methods for development of inbred corn lines and corn hybrids. Reference is made particularly to Corn and Corn Improvement, Third Edition, eds. G. F. Sprague and J. W. Dudley, American Society of Agronomy Monograph No. 18, particularly chapters 8 and 9.

SUMMARY OF THE INVENTION

According to the invention, there is provided a novel inbred corn line (948), designated NP 948. This invention thus relates to the seeds of inbred corn line NP 948, to the plants of inbred corn line NP 948 and to methods of producing a corn plant comprising the crossing of inbred line NP 948 with itself or another corn line. This invention further relates to hybrid corn seeds and plants produced by crossing the inbred line NP 948 with another corn inbred line.

DEFINITIONS

In the description and examples that follow a number of terms are used; therefore, to provide a clear and consistent understanding of the specification and claims the following definitions are provided.

RK=Round Kernels: the percentage of kernels that do not pass through a 13/64 slotted screen.

HE=Husk Extension: the length (cm) of the husk past the ear tip at maturity.

LL=Leaf Length: the length of the ear leaf measured in cm.

NN=Node Number: the number of nodes of the entire plant.

PRM=Predicated Relative Maturity. This trait is based on the harvest moisture of the grain. The relative maturity rating is based on a known set of checks.

MST=Harvest Moisture. The moisture is the actual percentage moisture of the grain at harvest.

STK (BR)=The percentage of plants broken below the ear at harvest.

YLD=Yield; bushels per acre. The actual yield of the grain at harvest (bu/a) adjusted to approximately 15.5% moisture.

RT=Number of plants lodged (leaning from vertical but not broken).

DETAILED DESCRIPTION OF THE INVENTION

Inbred corn line NP 948 is a yellow dent inbred line with superior characteristics and is best suited as a male in crosses for production of first generation $F_1$ corn hybrids. NP 948 is best adapted to the North Central part of the United States.

Inbred corn line NP 948 was developed from the backcross population (NP 807*1×L8401) by self-pollination and simple pedigreed ear-to-row breeding.

NP 807 is a Northrup King Co. proprietary line and L8401 is a line derived from the commercial hybrid Pioneer 3906. Self-pollination and selection were practiced within the above $F_1$ cross for seven generations in the development of NP 948. During the development of the line, crosses of segregating families were made to inbred testers to evaluate combining ability. Inbred line NP 948 can be reproduced by planting seeds of the line, growing the resulting corn plants under self-pollination or sib-pollination conditions with adequate isolation and then harvesting the resulting seed.

The inbred line has been evaluated at numerous research stations across the Northern United States Corn Belt and Canada. Inbred line NP 948 has shown uniformity and stability for all discernible characteristics as described in the following variety description. The description is based on data collected primarily at Stanton, Minn. and London, Ontario on a maximum of 9 replications.

TABLE 1

VARIETY DESCRIPTION
INFORMATION FOR INBRED LINE NP 948

Type: Dent     Region Best Adapted: North Central
A. Maturity:

Heat Units to Silk (HUS): 1336

$$\text{Heat Units} = \frac{\text{Max Temp}(\leq 86° \text{ F.}) + \text{Min Temp }(\geq 50° \text{ F.})}{2} - 50$$

B. Plant Characteristics:

Plant height (to tassel tip): 188 cm
Length to top ear internode: 13 cm
Ear height (to base of top ear internode): 63 cm
Number of tillers: none
Number of ears per stalk: slight two-ear tendency
Cytoplasm type: normal C. Leaf:

Color: dark green (B14)

TABLE 1-continued

VARIETY DESCRIPTION INFORMATION FOR INBRED LINE NP 948

Angle from stalk (upper half): 30–60 degrees
Number of leaves (mature plants): 12
Marginal waves: few
Width (widest point of ear node leaf): 8 cm
Sheath Pubescence: medium
Longitudinal creases: few
Length (ear node leaf): 63 cm D. Tassel:

Number of lateral branches: 6
Branch angle from central spike: 30–40 degrees
Pollen shed: medium
Peduncle length (top leaf to basal branch): 9 cm
Anther color: purple
Glume color: purple shading on green glumes E. Ear (Husked ear data except where stated otherwise):

Length: 13 cm
Weight: 89 gm
Midpoint diameter: 39 mm
Kernel rows: 14
Silk color: green
Husk extension: medium
Husk leaf: short (<8 cm)
Taper of ear: average
Position of shank (dry husks): pendent
Husk color (fresh): light green
Husk color (dry): buff
Shank length: 9 cm
Shank (no. of internodes): 8

F. Kernel (Dried):

Size (from ear mid-point):
Length: 10 mm
Width: 7 mm
Thickness: 4 mm
Shape grade (% rounds): 20–40
Pericarp color: colorless
Aleurone color: white
Endosperm color: yellow
Endosperm type: normal starch
Gm weight/100 seeds (unsized): 24

G. Cob:

Diameter at mid-point: 25 mm
Strength: strong
Color: red

H. Disease Resistance:
(0 = Not Tested; 1 = Susceptible; 2 = Resistant)

Stalk rot (Diplodia): 2
Northern leaf blight: 1
Stalk rot (Fusarium): 2
Corn smut: 2
Stalk rot (Giberella): 2
Smut: 2

I. Insect Resistance:

European corn borer: susceptible

J. Variety Most Closely Resembling:

| Character | Inbred |
|---|---|
| Maturity | NP807 |
| Usage | NP807 |

Line NP 807 is a Northrup King proprietary inbred (PVP Certificate No. 8700151). Inbred corn line NP 948 may be distinguished from corn line NP 807 by characteristics depicted in Table 2.

TABLE 2

Inbred Comparison Data of Inbred Line NP 948 and Inbred NP 807

| Line | RK% | HE (cm) | LL (cm) | NN |
|---|---|---|---|---|
| 948 | 29 | 5 | 63 | 13 |
| 807 | 63 | 8 | 69 | 11 |
| LSD (0.05) | 14 | 2 | 4 | 1 |

Data from 1994 at 3 locations (London, Ontario; Stanton, Minnesota and Janesville, Wisconsin); and 9 replications.

This invention is also directed to methods for producing a corn plant by crossing a first parent corn plant with a second parent corn plant, wherein the first or second corn plant is a corn plant of the inbred line NP 948. Therefore any methods using NP 948 are part of this invention including self-pollination, backcross-pollination, hybrid breeding and crosses to populations. Any plants produced using inbred corn line NP 948 as a parent are within the scope of this invention including any plant produced by the use of cells, protoplasts or tissue from NP 948.

An example of a hybrid produced by crossing inbred line NP 948 is N2555. This hybrid has NP 948 as a male parent and Northrup King inbred line NP 904 as a female parent. Inbred NP 904 has PVP Certificate No. 9200123. The techniques used to obtain the corn hybrid seeds and plants are conventional in the seed industry and are well known to those skilled in the art. The two parent varieties were planted in pollinating proximity to each other in alternating sets of rows; however, any convenient planting pattern that allows for the free transfer of pollen is acceptable. The plants of both inbred lines are allowed to grow until the time of flowering. At flowering, tassels are removed from all plants of the female parent by hand, machine or other means. Natural cross-pollination is allowed to occur. Ears from the female plants, NP 904, are harvested to obtain novel $F_1$ hybrid corn seeds N2555 of the present invention. $F_1$ hybrid corn plants of the invention are obtained by planting seeds of N2555.

N2555 is a 90 Minnesota relative maturity (RM) single cross hybrid. N2555 most closely resembles Northrup King Co. hybrid N2409. N2409 is a Northrup King Co. hybrid sold in the Northern U.S. and Canada. N2555 has significantly higher yield performance, significantly lower harvest moisture and improved stalk quality compared to N2409. In Table 3 below N2555 is compared to N2409 as a test hybrid.

TABLE 3

Combined Location and Year Performance Data (1992–1993; 56 environments; 85–100 RM Markets)

| Hybrid | YLD (bu/a) | MST | STK (BR) % | RT | HUS |
|---|---|---|---|---|---|
| N2555 | 140 | 23.9 | 3 | 2 | 1184 |
| N2409 | 131 | 24.6 | 5 | 1 | 1173 |
| LSD | 4 | 0.6 | 1 | 1 | 51 |

N2555 may be further described by characteristics listed in Table 4.

TABLE 4

VARIETY DESCRIPTION INFORMATION FOR HYBRID N2555

A. General: Type - single cross

Kernel Type - Dent
Maturity: Northrup King Maturity Zone 2;

Relative Maturity (RM): 88–90 days
U.S. Heat Units = 2650–2900
FAO = 250–350
Cytoplasm Type; normal B. Preflowering:

Length of first leaf blade; medium
Anthocyanic pigment of seedling; none or weak
Juvenile plant:

color: medium green
form: planofil
size: medium

C. Flowering

Number of leaves:

below ear: 6
above ear: 6
Leaf angle from stalk: 30–60 degrees
Leaf:

marginal waves: few
longitudinal creases: few
color:    dark
Number of tillers: None
Plant height to tassel tip: 253 cm
Length of top ear internode: 18 cm
Second internode:

width: 23 mm
length: 8 cm
Anthocyanic pigment of brace roots: weak or absent
Shape of tassel: loose
Number of lateral tassel branches: 9
Tassel branch angle: 30–45 degrees from vertical
Length of largest tassel branch: medium
Anther color: purple
Heat units to:

50% pollen shed: 1288
50% silk: 1302
Silk:

color: green
length outside of husk: 7 cm
Fresh husk color: light green
Ear leaf:

anthocyanic pigment; weak or none
pubescence: light
sheath pubscence: medium
length: 80 cm
width: 10 cm
Ear height: 87 cm
Number of:

nodes: 13
anthocyanic nodes: 2
anthocyanic internodes: 2
nodes with adventitious roots: 1
Peduncle length: 10 cm
Central spike length: long
Glume:

color: purple shading on green glumes
band color: purple
Pollen shed: medium
% of plants with ear wings: 38
Ear wing length: 4 cm
Number of ears per stalk: slight two-ear tendency

TABLE 4-continued

VARIETY DESCRIPTION INFORMATION FOR HYBRID N2555

D. Maturity

Husk:

extension: 2 cm
at maturity: flared
Shank:

length: 11 cm
internode number: 7
Kernel:

rows: distinct
alignment: straight
row number: 16
Ear weight: 160 gm
Kernel:

100 weight: 27 gm
length: 12 mm
width: 7 mm
thickness: 5 mm
% round kernels: 9
Ear:

position at maturity: pendent
length: 17 cm
diameter: 42 mm
taper: average
Cob:

color: red
diameter: 27 mm
strength: strong
Kernel color:

pericarp: colorless
aleurone segregation: homozygous
aleurone: white
endosperm: yellow
kernel crown: light yellow
kernel body (sides): yellow
Endosperm type: normal
% of kernels showing purple plumule tip: none Another hybrid produced by crossing of corn line NP 948 is Northrup King N3030. This hybrid has NP 948 as a male parent and Northrup King inbred line NP 912 as a female parent, and was produced using the techniques described above. Inbred line 912 has PVP Certificate No. 9200013. Hybrid N3030 may be further characterized by the following characteristics.

TABLE 5

VARIETY DESCRIPTION INFORMATION FOR HYBRID N3030

A. General: type - single cross

Kernel type - Dent
Maturity: Northrup King Maturity Zone 2;

Relative Maturity (RM); 90–95 days
U.S. Heat Units = 2400–2480
FAO = 250–350
Cytoplasm Type; normal B. Preflowering:

Length of first leaf blade: medium
Anthocyanic pigment of seedling: none or weak
Juvenile plant:

color: medium green

TABLE 5-continued

VARIETY DESCRIPTION INFORMATION FOR HYBRID N3030 form: compact
    size: medium
C. Flowering

Number of leaves:

below ear: 5
above ear: 6
Leaf angle from stalk: 30–60 degrees
Leaf:

marginal waves: few
longitudinal creases: few
color: dark
Number of tillers: none
Plant height to tassel tip: 265 cm
Length of top ear internode: 18 cm
Second internode:

width: 22 mm
length: 8 cm
Anthocyanic pigment of brace roots: weak or absent
Shape of tassel: loose
Number of lateral tassel branches: 8
Tassel branch angle: 30–45 degrees
Length of largest tassel branch: medium
Anther color: purple
Heat units to:

50% pollen shed: 1292
50% silk: 1291
Silk:

color: green with pink ends
length outside of husk: 9 cm
Fresh husk color: light green
Ear leaf:

anthocyanic pigment: weak or none
pubescence: medium
sheath pubescence: medium
length: 80 cm
width: 10 cm
Ear height: 86 cm
Number of:

nodes: 13
anthocyanic nodes: 2
anthocyanic internodes: 2
nodes with adventitious roots: 1
Peduncle length: 12 cm
Central spike length: long
Glume:

color: green with purple shading
band color: green
Pollen shed: medium
% of plants with ear wings: 32
Ear wing length: 3 cm
Number of ears per stalk: slight two-ear tendency
D. Maturity Husk:

extension: 3 cm
at maturity: flared
Shank:

length: 13 cm
internode number: 7
Kernel:

rows: distinct
alignment: straight
row number: 16
Ear weight: 155 gm

TABLE 5-continued

VARIETY DESCRIPTION INFORMATION FOR HYBRID N3030

Kernel:

100 weight: 27 gm
lenghth: 11 mm
width: 8 mm
thickness: 5 mm
% round kernels: 13
Ear position at maturity: pendent
length: 17 cm
diameter: 43 cm
taper: slight
Cob:

color: red
diameter: 27 mm
strength: strong
Kernel color:

pericarp: colorless
aleurone segregation: homozygous
aleurone: white
endosperm: yellow
kernel crown: light yellow
kernel body (sides): yellow
Endosperm type: normal
% of kernels showing purple plumule tip: 1

---

As used herein the term plant includes plant cells, plant protoplasts, plant cell tissue cultures including that from which corn plants fertile or otherwise can be regenerated, plant calli and plant cell clumps, and differentiated forms of plants such as, but not limited to embryos, pollen, stamen, anthers, flowers, kernels, ears, cobs, leaves, stalks, roots, shoots, plantlets, silks and kernels.

Methods of cell and tissue culture and regeneration are well known in the art and described for example in "Plant Tissue Culture Manual: Fundamentals and Application", Ed. K. Lindsey, Kluwer (1991) and in Green and Rhodes, "Plant Regeneration in Tissue Culture of Maize", Maize for Biological Research (Plant Molecular Biology Association, Charlottesville, Va., 1982, pp. 367–372), which are hereby incorporated by reference.

As is well known corn can be put to a wide variety of uses not only as livestock feed but also for human consumption of corn kernels and as a raw material in industry. Both grain and non-grain portions of the plant are used as a livestock feed for swine, cattle and poultry. In the food industry corn is used in wet and dry milling. In wet milling there is the separation of the germ, hull gluten and starch. Germ is used to produce corn oil and germ cake for feed. Corn starch may be packaged for human consumption or used in food products such as sauces, gravies, puddings, sweeteners, syrups, and baking powder. Other nonedible uses include textiles, paper, adhesives, cosmetics, explosives, corn binders, laundry purposes and agricultural formulations. Dry milling is used to produce breakfast foods, grits, cornmeal and corn flour. Other uses of corn include fuel, in the form of fuel alcohol or ethanol; seed; alcoholic beverages and construction.

DEPOSIT INFORMATION

Deposits of at least 2500 seeds each of inbred NP 948, hybrid N2555 and hybrid N3030 have been made unrestrictedly available to the public via the American Type Culture Collection (ATCC), Rockville, Md. 20852 USA. The deposit of 2500 seeds of the NP 948 was made on Oct. 21, 1997 pursuant to the Budapest Treaty and accorded the deposit number ATCC 209406. The deposits of 2500 seeds each of the two hybrids and their female parents (NP 904 and NP 912) pursuant to the Budapest treaty were made on Nov. 14, 1997. NP912 was accorded ATCC Deposit No. 209457; NP904 was accorded ATCC Deposit No. 209458; N2555 was accorded ATCC Deposit No. 209459; and N3030 was accorded ATCC Deposit No. 209460. The seeds are from stock maintained by Northrup King since prior to filing this application or any parents thereof. Additionally, a Plant Variety Protection Certificate has been applied for with the United States Department of Agriculture. Additionally, with respect to Plant Variety Protection Certificates received and applied for, Applicant does not waive any infringement of its rights granted under this patent or under the Plant Variety Protection Act (7 U.S.C. 2312 et seq.).

What is claimed is:

1. Inbred corn seed designated NP 948 having ATCC Accession No. 209406.

2. A corn plant produced by growing the seed of claim 1.

3. A corn plant having all physiological and morphological characteristics of the plant of claim 2.

4. Pollen of the plant of claim 2.

5. A tissue culture comprising regenerable cells of the plant according to claim 2.

6. A corn plant regenerated from the tissue culture of claim 5, said plant having all the physiological and morphological characteristics of inbred corn plant NP 948, the seed of which has been deposited under ATCC Accession No. 209406.

7. $F_1$ generation hybrid corn seed designated N2555 having ATCC Accession No. 209459.

8. $F_1$ generation hybrid corn plants N2555 produced by growing the seed of claim 7.

9. Seeds produced by the cultivation of the corn plants of claim 8.

10. Hybrid corn seed designated N2555 produced by:
   a. planting in pollinating proximity seeds of inbred corn lines NP 948 (ATCC Accession No. 209406) and NP 904 (ATCC Accession No. 209458);
   b. cultivating corn plants resulting from said planting until time of flowering;
   c. emasculating said flowers of plants of inbred line NP 904;
   d. allowing cross pollination to occur between said inbreds; and
   e. harvesting the seeds produced on said plants of inbred line NP 904.

11. $F_1$ generation hybrid corn seed designated N3030 having ATCC Accession No. 209460.

12. $F_1$ generation hybrid corn plants N3030 produced by growing the seeds of claim 11.

13. Seeds produced by the cultivation of the corn plants of claim 12.

14. Hybrid corn seed designated N3030 produced by:
   a. planting in pollinating proximity seeds of inbred corn lines NP 948 (ATCC Accession No. 209406) and NP 912 (ATCC Accession No. 209457);
   b. cultivating corn plants resulting from said planting until time of flowering;
   c. emasculating said flowers of plants of inbred line NP 912;
   d. allowing cross pollination to occur between said inbreds; and
   e. harvesting the seeds produced on said plants of inbred line NP 912.

15. Hybrid corn plants produced by crossing plants of inbred corn line NP 948, the seed having ATCC Accession No. 209406, and plants of another inbred corn line having a genotype different from corn line NP 948.

16. A first generation (F1) hybrid corn plant produced by growing said hybrid corn seed of claim 15.

17. A tissue culture of regenerable cells of the corn plant of claim 16.

18. Hybrid seed of claim 15 wherein corn line NP 948 is the male parent.

* * * * *